(12) United States Patent
Williams

(10) Patent No.: US 6,245,348 B1
(45) Date of Patent: Jun. 12, 2001

(54) TOPICAL, THERAPEUTIC COMPOSITION FOR EXTERNAL USE AND METHOD OF TREATMENT

(76) Inventor: Timothy Williams, 624 Kingsgate Ridge, Stone Mountain, GA (US) 30088

( * ) Notice: Subject to any disclaimer, the term of this patent is extended or adjusted under 35 U.S.C. 154(b) by 0 days.

(21) Appl. No.: 09/370,110

(22) Filed: Aug. 6, 1999

Related U.S. Application Data

(63) Continuation-in-part of application No. 09/084,489, filed on May 26, 1998, now abandoned.

(51) Int. Cl.[7] ............................................. A61F 13/00
(52) U.S. Cl. ........................... 424/449; 424/484; 514/557; 514/724
(58) Field of Search ..................................... 424/449, 484; 514/557, 724

(56) References Cited

U.S. PATENT DOCUMENTS 5,560,916 * 10/1996 Koulbanis et al. .................. 424/401
5,616,619 * 4/1997 Stofer .................................. 514/574

* cited by examiner

Primary Examiner—Kevin E. Weddington
(74) Attorney, Agent, or Firm—Gardner Groff Mehrman & Josephic

(57) ABSTRACT

A topical, therapeutic composition is disclosed which is useful in relieving inflammatory muscular discomfort in a human being. The composition comprises: at least one of cider vinegar and red vinegar; isopropyl alcohol; and ethyl alcohol which are mixed with bleach flour and corn starch to form a paste which is applied to the human being at an area of inflammatory discomfort. Also disclosed is a method of relieving inflammatory muscular discomfort in a human being comprising the steps of: applying a paste, comprising at least one of cider vinegar and red vinegar; isopropyl alcohol; and ethyl alcohol, mixed with bleach flour and corn starch to form the paste, to the human being at an area of inflammatory discomfort; covering the applied paste with a cloth; loosely wrapping the area of inflammatory discomfort; and allowing the applied paste to remain on the area of inflammatory discomfort overnight.

19 Claims, 2 Drawing Sheets

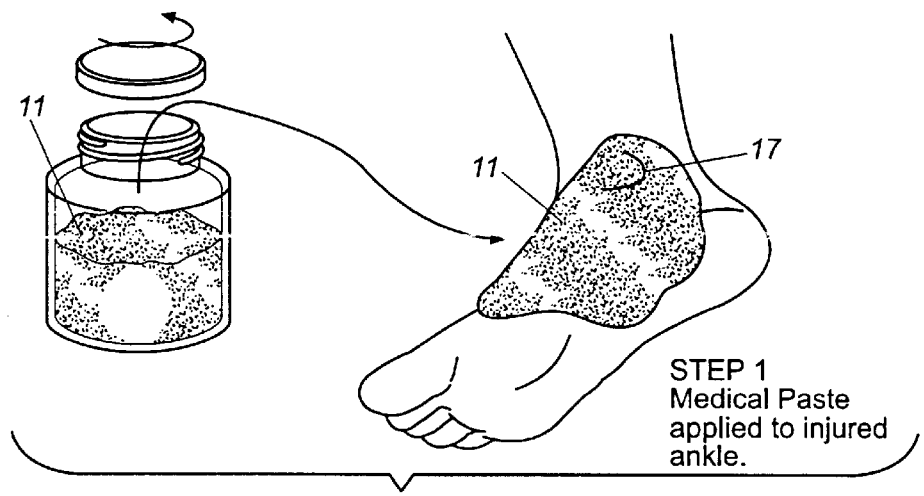
STEP 1 Medical Paste applied to injured ankle.
Fig. 2A
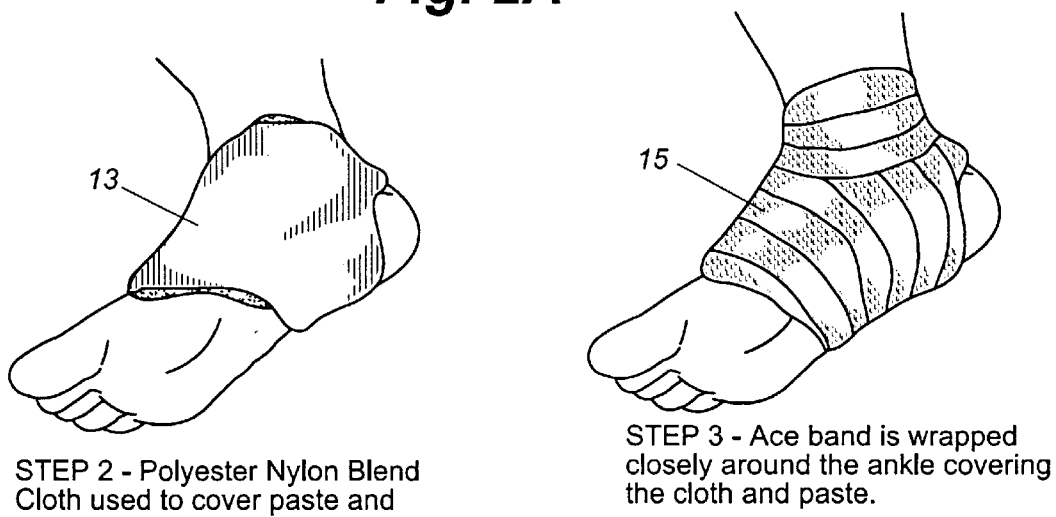
STEP 2 - Polyester Nylon Blend Cloth used to cover paste and injured ankle.
Fig. 2B
STEP 3 - Ace band is wrapped closely around the ankle covering the cloth and paste.
Fig. 2C
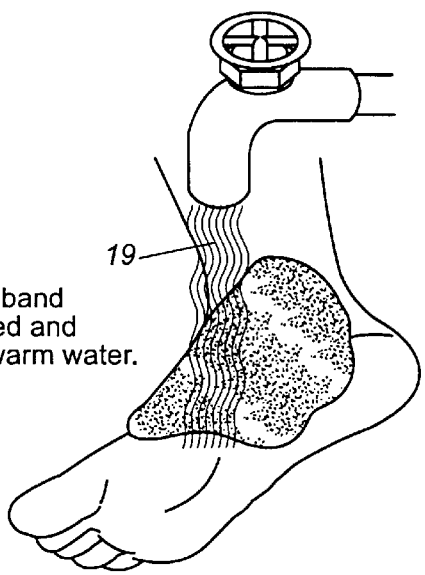
STEP 4 - Next day ace band removed, cloth discarded and paste washed off with warm water.
Fig. 2D

TOPICAL, THERAPEUTIC COMPOSITION FOR EXTERNAL USE AND METHOD OF TREATMENT

This is a continuation-in-part application of application Ser. No. 09/084,489, filed May 26, 1998 now abandoned.

BACKGROUND OF THE INVENTION

1. Field of the Invention

The present invention generally relates to a beneficial, topical composition that is particularly useful in relieving muscular discomfort experienced by a human being as a result of strenuous physical activity as well as a method of treatment therewith.

2. Background Discussion

Participation in strenuous physical activities, such as sports, oftentimes results in muscular related discomfort such as stiffness, pain, swelling and soreness in both shallow and deep muscle tissues. Therefore, professional and non-professional athletes require effective ways to treat muscular-type injuries and provide fast acting relief as well as shorten the time of recovery.

In addition, inflammatory skeletal muscle conditions, such as, for example, arthritis, bursitis, strains, and sprains cause similar muscular related distress and hinder physical movements. As a result, there is also a requirement for temporary relief and treatment of the associated everyday pain of such inflammatory skeletal muscle conditions.

Theretofore, analgesics, which are ingested every four hours, such as aspirin, have been used, however, gastrointestinal discomfort is a possible side-effect. In addition, ointments, balms, rubs, gels and creams, which are applied topically to the effected area several times a day, can be used. However, due to the rapid evaporation into the atmosphere of volatile constituents contained therein, effective treatment is minimized and recovery time increased.

SUMMARY OF THE INVENTION

Accordingly, it is an object of the present invention to provide a beneficial, topical composition which is useful in relieving pain, swelling, stiffness and soreness, in both deep and shallow muscles, resulting from strenuous physical activities.

One particularly advantageous feature of the present invention is that the topical composition can be formulated as a paste for extended external application to an area of the body experiencing pain, swelling, stiffness and soreness. The paste formulation inhibits evaporation of active ingredients contained therein and concentrates the beneficial components of the composition at the affected area without the need to soak the injured area in the active ingredients during treatment.

Another advantageous feature of the present invention is that the beneficial, topical composition is relatively easy and inexpensive to manufacture with basic factory mixers and readily available ingredients.

Further, the present invention is not only useful in reducing swelling, soreness, pain, stiffness, in deep and shallow muscles, to relieve the discomfort occasioned from participation in strenuous physical activities such as sports, it is also useful in treating inflammatory skeletal muscle conditions, such as, for example, arthritis, bursitis, strains, and sprains.

Since, according to the preferred embodiment of the present invention, the topical composition is formulated as a paste, it solidifies after application to the body thereby concentrating the active ingredients on the affected area to provide fast acting, maximum treatment and decreasing the time of recovery. Moreover, in a contradistinction to prior art approaches which require multiple daily applications, the beneficial composition of the present invention need be applied only once a day in order to be effective.

These and other objects, advantages and features of the present invention are achieved by utilizing a topical, therapeutic composition that comprises, in its broadest formulation, red or cider vinegar or mixtures thereof combined with ethyl alcohol and isopropyl alcohol.

When the therapeutic composition is formulated as a paste, it is applied directly to the injury, covered with a cloth material and wrapped loosely with an ace bandage. After application, the paste hardens and remains on the injured part of the body overnight in order to provide the affected area maximum treatment thereby reducing the time of recovery. In the morning, the hardened paste, which is water soluble, is easily washed off with water.

Therefore, according to a first preferred embodiment of the present invention, the topical composition comprises: red or cider vinegar or mixtures thereof, combined with alcohol, for example, isopropyl alcohol and/or ethyl alcohol to form an aqueous solution which mixed with an inert matrix material to form a paste, the inert matrix material comprising, for example, flour, starch and petroleum jelly. The resulting composition is then applied to the affected area of the body in accordance with the method of the present invention.

According to a further embodiment, an extra strength composition is formulated by adding a small amount of dissolved magnesium sulfate (approximately 70% solution) and cetyl alcohol to the formulation of the first embodiment.

In a third embodiment, for severe injuries, the composition comprises ethyl alcohol, red or cider vinegar or mixtures thereof, isopropyl alcohol, methanol, stearyl alcohol, triethanolamine and in an inert matrix material of, for example, bleached flour and corn starch.

According to yet another embodiment of the present invention, the therapeutic composition comprises a combination of petroleum jelly, wheat flour, gloss starch, apple cider vinegar, pure vanilla extract, ethyl alcohol, isopropyl alcohol and mineral oil.

In each of the embodiments noted above, fragrances can be added to the therapeutic composition.

BRIEF DESCRIPTION OF THE DRAWINGS

FIGS. 2A, 2B, 2C and 2D illustrate steps of the method of treatment of an injured area of the body according to the present invention.

DETAILED DESCRIPTION OF THE PREFERRED EMBODIMENT(S)

Figure 1A:
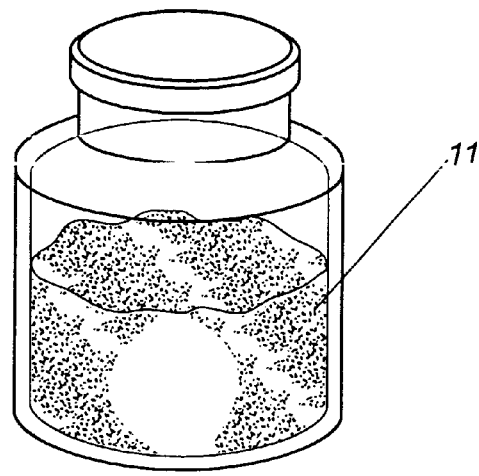
FIGS. 1A, 1B and 1C illustrate the various components used to treat an injured area of the body according to the present invention.
Figure 1B:
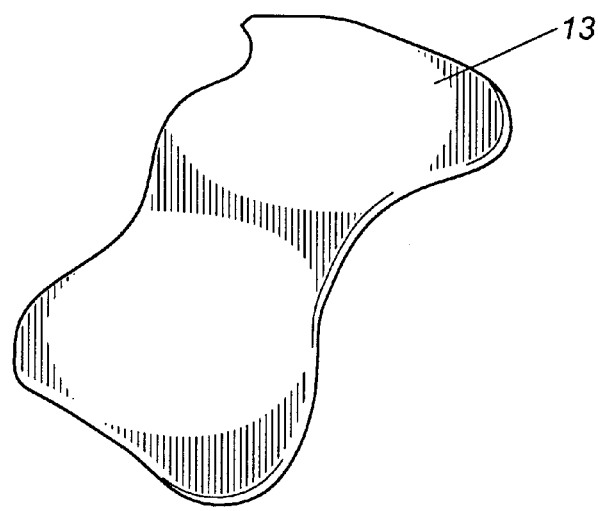
Figure 1C:
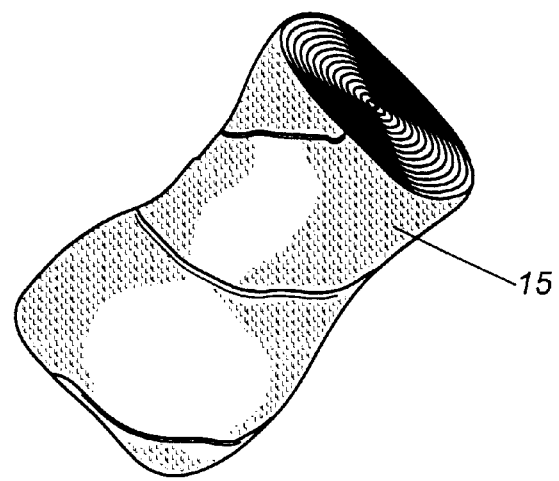

Referring to FIGS. 1A, 1B, and 1C, the various elements of the present invention are shown for treating an area of the human body which is experiencing muscular discomfort in accordance with the method of the present invention. The muscular discomfort comprises, for example, stiffness, pain, swelling and soreness in both shallow and deep muscle tissues occasioned from strenuous physical activity, such sport, as well as skeletal muscle conditions, such as, for example, arthritis, bursitis, strains, and sprains. The invention is useful in reducing swelling, pain and/or soreness, provides fasting relief and reduces the time of recovery from injury.

As shown in FIGS. 1A, 1B, and 1C, the method of the present invention uses a beneficial and therapeutic composition 11 in paste form, a covering material 13, such as, for example, a cloth or fabric material as well as a plastic sheet material, and an elastic wrap 15, such as, for example, an ace bandage or the like.

Referring to FIGS. 2A, 2B, 2C and 2D, the method of treatment according to the present invention is illustrated. In step one, the therapeutic paste 11 is applied to an area 17 of the body experiencing pain, swelling and/or soreness. Once the paste 11 is applied, the covering material 13, for example, polyester nylon blend cloth 17 is used to cover the paste 11. In step three, the elastic wrap 15, such as an ace bandage, is wrapped loosely around the injured area covering the covering material 13 and the paste 11 and allowed to sit overnight. In step 4, the ace bandage 15 and cloth 13 are removed and the paste 11 is washed off with warm water 19.

The therapeutic paste 11, according to a first embodiment, comprises an aqueous solution of: red vinegar or cider vinegar (for example, apple cider vinegar) or mixtures thereof combined with alcohol, for example, a mixture of ethyl alcohol and isopropyl alcohol. The aqueous solution is mixed with a substantially inert matrix material (does not react with active ingredient) to form a paste, the matrix material comprising, for example, flour, starch and petroleum jelly.

While the present invention is effective in reducing swelling, pain swelling, and/or soreness when red or cider vinegar or mixtures thereof is the only active ingredient, the effectiveness of the therapeutic composition is increased when the alcohols are also included as part of the aqueous solution combined with the matrix material to form the paste 11.

According to a further embodiment, an extra strength composition is formulated by adding a small amount of dissolved magnesium sulfate (approximately 70% solution) and cetyl alcohol to the formulation of the first embodiment.

According to a third embodiment, for severe injuries, the composition comprises ethyl alcohol, red or cider vinegar or mixtures thereof, isopropyl alcohol, methanol, stearyl alcohol, triethanolamine and in an inert matrix material of, for example, bleached flour and corn starch.

According to yet another embodiment of the present invention, the therapeutic composition comprises a combination of petroleum jelly, wheat flour, gloss starch, apple cider vinegar, pure vanilla extract, ethyl alcohol, isopropyl alcohol and mineral oil. By way of example, this embodiment of the therapeutic composition is made from about 30.63 grams of petroleum jelly, about 84.48 grams of 100% wheat flour, about 100.43 grams of gloss starch, about 124.0 milliliters of apple cider vinegar, about 30.50 milliliters of pure vanilla extract, about 11.0 milliliters of 70% ethyl alcohol, about 19.0 milliliters of 70% isopropyl alcohol and about 5.0 milliliters of mineral oil.

According to one embodiment of making the therapeutic composition, the aqueous solution of red or cider vinegar or mixtures thereof and ethyl and isopropyl alcohol is first mixed with the flour of the matrix material at a relatively slow speed until fully blended and allowed to stand for a short period of time. The starch is added last and mixed at a substantially medium speed until the paste has a consistent blend. The paste is then packaged in a sealed container, for example, plastic jar or tube, for sale.

EXAMPLE 1

Active ingredients—62 milliliters of isopropyl alcohol, 62 milliliters of ethyl alcohol and 124 milliliters of red vinegar. Matrix material—5.7 grams of starch, for example, corn starch and 171.5 grams of bleached flour to form a paste. The composition is made by weighing 171.5 grams of white bleach to which is added 124 milliliters of red vinegar and mixed at a relatively slow speed until fully blended, i.e., about one and a half minutes. The alcohols (62 milliliters of isopropyl alcohol and 62 milliliters of ethyl alcohol) are then added and mixed at a relatively low speed until fully blended, i.e., about three minutes. 5.7 grams of starch are added to the paste and mixed until the product has a consistent blend, i.e., about one and a half minutes.

EXAMPLE 2

Active ingredients—31 milliliters of ethyl alcohol, 62 milliliters of isopropanol, 1.5 milliliters of dissolved magnesium sulfate (approximately 70% solution), 1.5 milliliters of cetyl alcohol, and 124 milliliters of cider vinegar. Matrix material—171.5 grams of bleached flour and 5.7 grams of corn starch. Mixed as noted in Example 1, i.e., cider vinegar and flour mixed first, then additional active ingredients added and finally starch is mixed to form a paste of a consistent blend.

EXAMPLE 3

Active ingredients—62 milliliters of ethyl alcohol, 55 milliliters of isopropanol, 1 milliliter of methanol, 1 milliliter of stearyl alcohol, 1 milliliter of triethanolamine, and 124 milliliters of cider vinegar. Matrix material—171.5 grams of bleached flour and 5.7 grams of starch, for example, corn starch. Mix as noted in Example 1, i.e., the cider vinegar and flour are mixed first, then other active ingredients are added and mixed, and then corn starch is mixed for form a paste of a consistent blend.

EXAMPLE 4

About 30.63 grams of petroleum jelly weighed using an analytical balance is transferred to a sterile stainless steel bowl and melted on a metal stand with the flame of a bunsen burner. About 73.50 grams of 100% wheat flour, about 86.30 grams of gloss starch are mixed slowly with a wooden spatula in a separate bowl until homogenous. About 124.0 milliliters of apple cider vinegar, about 11.0 milliliters of 70% ethyl alcohol, about 19.0 milliliters of 70% isopropyl alcohol, and about 20.50 milliliters of pure vanilla extract (collectively referred to as the "aqueous solution") are measured using a graduated cylinder and mixed for about 1.0 minutes in a 600.0 milliliter glass beaker using a glass stirring rod. The aqueous solution is added to the starch, flour mixture and mixed well to a paste of uniform consistency. During the mixing step, the paste is heated and blended simultaneously with, for example, an industrial mixer on a high setting for about 3.2 minutes and then removed from the heat and covered.

Once the petroleum jelly reaches room temperature, the petroleum jelly is added to the paste and blended using the high setting of the industrial mixer for about 3.0 minutes. The paste is covered for about 1.5 minutes. Then, about 3.76 grams of 100% wheat flour, about 4.71 grams of gloss starch, and about 5.0 milliliters of pure vanilla extract are added to the paste and blended slowly until well blended. Finally, about 7.52 grams of wheat flour and about 9.42 grams of gloss starch, as well as about 5.0 milliliters of pure vanilla extract and about 5.0 milliliters of mineral oil are added and blended at low speed for about one minute.

Methyl salicylate and fragrances can also be added to each of the formulations noted above.

Although the present invention has been described with particular reference to its preferred embodiments, it should be understood that many variations and modifications will now be obvious to those skilled in that art, and it is preferred, therefore, that the scope of the invention be limited, not by the specific disclosure herein, but only by the appended claims.

What is claimed is:

1. A topical, therapeutic composition useful in relieving stiffness, pain, swelling and soreness in both shallow and deep muscles of a human being resulting from strenuous physical activity, the composition comprising:

an aqueous solution comprising cider vinegar, red vinegar, or a mixture thereof, and a mixture of isopropyl alcohol and ethyl alcohol; and an inert matrix material comprising flour, starch, or a mixture thereof, wherein the inert matrix material is mixed with the aqueous solution to form a paste that is applied to an area of the human being experiencing the stiffness, pain, swelling and soreness.

2. A composition according to claim 1, further comprising a fragrance, and wherein the inert matrix material further comprises mineral oil, petroleum jelly or a mixture thereof.

3. A composition according to claim 2, further comprising magnesium sulfate and cetyl alcohol.

4. A composition according to claim 2, further comprising methanol, stearyl alcohol, and triethanolamine.

5. A composition according to claim 2, further comprising cetyl alcohol.

6. A composition according to claim 2, further comprising methyl salicylate.

7. A composition according to claim 1, comprising equal amounts of the cider or red vinegar, or a mixture thereof and the mixture of isopropyl alcohol and ethyl alcohol.

8. A method of relieving stiffness, pain, swelling and soreness in both shallow and deep muscle tissues of a human being resulting from strenuous physical activity, the method comprising the steps of:

applying a paste, comprising red or cider vinegar or mixtures thereof and at least one alcohol to form an aqueous solution which is mixed with an inert matrix material to form the paste, to the human being at an area of stiffness, pain, swelling and soreness resulting from the strenuous physical activity;

covering the applied paste with a cloth;

loosely wrapping the area; and allowing the applied paste to remain on the area overnight.

9. A method according to claim 8, wherein the paste further comprises a fragrance, the at least one alcohol comprises a mixture of isopropyl alcohol and ethyl alcohol, and the inert matrix material comprises at least one of flour, starch, mineral oil and petroleum jelly.

10. A method according to claim 9, wherein the paste further comprises magnesium sulfate and cetyl alcohol.

11. A method according to claim 9, wherein the paste further comprises methanol, stearyl alcohol, and triethanolamine.

12. A method according to claim 9, wherein the paste further comprises cetyl alcohol.

13. A method according to claim 9, wherein the paste further comprises methyl salicylate.

14. A topical, therapeutic composition useful in relieving stiffness, pain, swelling and soreness in both shallow and deep muscles of a human being resulting from strenuous physical activity, the composition consisting essentially of: (i) an aqueous solution comprising cider or red vinegar, or a mixture thereof, isopropyl alcohol, and ethyl alcohol; and mixed therewith (ii) a fragrance and (iii) an inert matrix material consisting essentially of flour, starch, mineral oil and petroleum jelly to form a paste that is applied to an area of the human being experiencing the stiffness, pain, swelling and soreness.

15. A composition according to claim 14, further consisting of magnesium sulfate and cetyl alcohol.

16. A composition according to claim 14, further consisting of methanol, stearyl alcohol, and triethanolamine.

17. A composition according to claim 14, further consisting of cetyl alcohol.

18. A composition according to claim 14, further consisting of methyl salicylate.

19. A composition according to claim 14, consisting of equal amounts of at least one of cider vinegar and red vinegar, and isopropyl alcohol and ethyl alcohol.

* * * * *